United States Patent [19]

Brown et al.

[11] Patent Number: 5,463,094
[45] Date of Patent: Oct. 31, 1995

[54] SOLVENT FREE QUATERNIZATION OF TERTIARY AMINES WITH DIMETHYLSULFATE

[75] Inventors: David M. Brown, Charlotte, N.C.; Erich M. Gatter, Kastl, Germany; Cheryl A. Littau, Charlotte, N.C.

[73] Assignee: Hoechst Celanese Corporation, Somerville, N.J.

[21] Appl. No.: 247,804

[22] Filed: May 23, 1994

[51] Int. Cl.$^6$ .................. C07C 219/02; C07C 209/00
[52] U.S. Cl. .......... 554/110; 554/109; 564/281; 564/285; 564/292; 564/294; 564/296
[58] Field of Search ............... 252/8.8; 558/27; 564/281, 291, 292, 296, 294, 285; 554/109, 110

[56] References Cited

U.S. PATENT DOCUMENTS

| | | | |
|---|---|---|---|
| 4,228,096 | 10/1980 | Bozzelli et al. | 558/28 |
| 4,237,064 | 12/1980 | Reck | 558/27 |
| 4,281,196 | 7/1981 | Rutzen et al. | 564/292 |
| 4,370,272 | 1/1983 | Wechsler et al. | 554/110 |
| 4,515,723 | 5/1985 | Billenstein et al. | 554/84 |
| 4,830,771 | 5/1989 | Ruback et al. | 554/110 |
| 4,923,642 | 5/1990 | Rutzen et al. | 554/110 |
| 4,954,635 | 9/1990 | Rosario-Jansen et al. | 548/354 |
| 4,982,000 | 1/1991 | Earl et al. | 564/296 |
| 5,116,520 | 5/1992 | Lichtenwalter et al. | 252/8.6 |
| 5,223,628 | 6/1993 | Whittlinger | 548/349.1 |
| 5,284,650 | 2/1994 | Whittlinger | 424/70 |
| 5,296,622 | 3/1994 | Uphues et al. | 554/110 |

FOREIGN PATENT DOCUMENTS

| | | |
|---|---|---|
| 375029 | 12/1989 | European Pat. Off. . |
| 387064 | 3/1990 | European Pat. Off. . |
| 409502 | 7/1990 | European Pat. Off. . |
| 409504 | 7/1990 | European Pat. Off. . |
| 420465 | 9/1990 | European Pat. Off. . |
| 145196 | 9/1982 | Japan . |
| 64-22337 | 1/1989 | Japan . |
| 264073 | 1/1990 | U.S.S.R. . |
| 9101295 | 2/1991 | WIPO . |
| 91/17974 | 11/1991 | WIPO ................... 554/109 |
| 94/14756 | 7/1994 | WIPO ................... 554/109 |
| 94/21592 | 9/1994 | WIPO ................... 554/110 |
| 94/21593 | 9/1994 | WIPO ................... 554/110 |

OTHER PUBLICATIONS

Bram, G., et al., "N–Alkylation of Pyrimidine and Purine Derivatives (Uracils, Xanthines, Adenine) Using Solid/Liquid Phase–Transfer Catalysis Without Solvent", *Synthesis*, (5), pp. 543–545 (1985) (no month).

Nametkin, N. S., et al., "Salts of Quaternary Ammonium Bases Obtained from Naphthenic Acids", *Neftekhimiya*, 12(6), pp. 894–897 (1972) (no month).

Vorona, N. I., et al., "Surface–Active Quaternary Ammonium Salts. 5. Synthesis and Properties of Salts of Chlorine Alkoxymethyl Ethers", *Izv. Vyssh. Uchebn. Zaved., Khim. Khim. Tekhnol.*, 19(6), pp. 876–880 (1976) (no month).

Bram, G., et al., "Efficient Synthesis of Alkylacetamidomalonates by Solid–Liquid Phasetransfer Catalysis Without Solvent", *Pharmazie*, 42(3), p. 199 (1987) (no month).

*Primary Examiner*—Anthony Green
*Attorney, Agent, or Firm*—Rosemary M. Miano

[57] ABSTRACT

A process for a high temperature, solvent free quaternization of certain tertiary amines using dimethylsulfate to produce quaternary ammonium methyl sulfates which may be used in fabric softening and other applications, is disclosed.

8 Claims, No Drawings

SOLVENT FREE QUATERNIZATION OF TERTIARY AMINES WITH DIMETHYLSULFATE

FIELD OF THE INVENTION

This invention is directed to a process for a high temperature, solvent free quaternization of certain tertiary amines using dimethylsulfate to produce quaternary ammonium compounds which can be useful in fabric softening and other applications.

BACKGROUND OF THE INVENTION

Quaternary ammonium compounds are well known for their use in fabric softening applications. It has been found that the quaternary ammonium fabric softening materials comprised of one or more $C_8$–$C_{28}$ alkyl or alkenyl groups connected to the softener molecule via an ester linkage are of particular importance because they are more biodegradable than conventional quaternary ammonium compounds. It is also known that fatty groups of $C_{16}$ to $C_{18}$ or longer are necessary to obtain optimum softening in these molecules.

These compounds can be prepared by a number of methods. For example, U.S. Pat. No. 4,515,723 discloses quaternary N-alkyl-N,N',N'-polyoxyalkyl-α,ω-diamino-alkylene fatty acid esters which are prepared by esterifying oxyalkylated fatty alkyl-alkylene diamines and quaternizing the reaction product with an alkylating agent. The quaternization disclosed therein can be carried out in water, in a solvent or without any solvent.

U.S. Pat. No. 4,228,096 claims a method of preparing quaternary ammonium salts from various morpholinones using, among others, dimethylsulfate as a quaternizing agent. This is a two step process in which the quaternization can be conducted either neat or in the presence of an inert solvent. The patent notes however that the quaternization step, V, is preferably conducted in the presence of a polar solvent such as tetrahydrofuran.

European Patent Application EP 0375029 to Procter & Gamble discloses process for preparing substituted imidazoline fabric conditioning compounds and is incorporated in it entirety by reference herein.

PCT Application WO 91/01295 to Truis, et al discloses a process for preparing quaternary ammonium compounds as fabric softeners.

It is an object of this invention to provide a solvent free process for the preparation of certain quaternary ammonium methyl sulfates.

The advantage of this novel process lies in both its economic and environmental importance. Without the use of solvent, the process is clearly less expensive than similar solvent requiring processes. Additionally, no waste solvent is generated with the requisite cost of cleanup or recycling. A further advantage to this solvent-free process is that for certain applications, the use of solvent free material is highly desirable and imparts special value to the end product. Still a further advantage of this process is that it reduces or eliminates the number of undesirable side reactions, such as transesterification, hydrolysis and/or methylation of solvent with the dimethylsulfate. Lastly, an additional advantage lies in the fact that the absence of solvent in the end product reduces or eliminates problems with flammability and/or toxicity associated with lower alkanol solvents such as ethanol, methanol or isopropanol.

SUMMARY OF THE INVENTION

This invention is directed to a process for the high temperature, solvent free quaternization of certain tertiary amines using dimethylsulfate. Generally, the tertiary amines are quaternized by the addition of dimethylsulfate to a solution of the stirred, molten tertiary amine under a blanket of an inert gas such as nitrogen or argon. The exothermic reaction increases the temperature of the final reaction mixture, which is maintained above the melting point of the final quaternized amine, until the dimethylsulfate has been consumed.

DESCRIPTION OF THE PREFERRED EMBODIMENTS

This invention relates to a process for the high temperature, solvent free quaternization of certain tertiary amines with dimethylsulfate. In particular, tertiary amines of the general formula I

wherein each of $R_1$, $R_2$ and $R_3$ can be independently selected from a) $C_1$–$C_{20}$ alkyl;
b) $C_2$–$C_{20}$ alkenyl;
c) $C_2$–$C_{20}$ alkynyl;
d) hydroxy $C_1$–$C_{20}$ alkyl;
e) dihydroxy $C_1$–$C_{20}$ alkyl;
f) poly(oxyethylene) of the formula —$(CH_2CH_2O)_xH$, where x is an integer from 1 to 20;
g) poly(oxypropylene) of the formula —$(CH_2CH(CH_3)O)_yH$, where y is an integer from 1 to 50;
h) copolymers of ethylene oxide and propylene oxide, arranged randomly, in alternating units, or in blocks, and terminated with either ethylene oxide or propylene oxide, wherein the total content of x and y is 70;
i) carboxylate esters of d, e, f and g above wherein the acyl chain of the carboxy function is $C_1$ to $C_{20}$ in length and can be saturated or unsaturated;
j) cyclo $C_3$–$C_8$ alkyl;
k) phenyl or substituted phenyl;
l) phenyl alkyl (e.g. benzyl or phenethyl);
m) heterocyclic rings of 3 to 7 members containing one nitrogen atom such that $R_1$ and $R_2$ are part of the same chain;
n) heterocyclic rings of 3 to 7 members containing two heteroatoms, one of which is nitrogen and the second is selected from N—, —O— or —S—, such that $R_1$ and $R_2$ are part of the same chain; examples of these include imidazole, morpholine, etc.;
o) substituted or disubstituted heterocyclic compounds of formula II

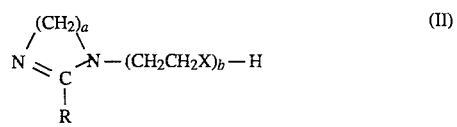

where
a=2, 3, 4, or 5;

b=1–20;

X=N or O;

R=hydrogen, $C_1$–$C_{20}$ alkyl, $C_2$–$C_{20}$ alkenyl or $C_2$–$C_{20}$ alkynyl;

p) substituted or disubstituted heterocyclic compounds of formula III

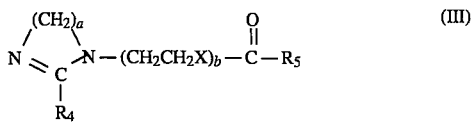
(III)

where a=2, 3, 4, or 5;

b=1–20;

X=N or O;

$R_4$=hydrogen, $C_1$–$C_{20}$ alkyl, $C_2$–$C_{20}$ alkenyl or $C_2$–$C_{20}$ alkynyl; and $R_5$=hydrogen, $C_1$–$C_{20}$ alkyl, $C_2$–$C_{20}$ alkenyl or $C_2$–$C_{20}$ alkynyl.

Preferred tertiary amines useful in the process of this invention include compounds of formula I wherein each of $R_1$, $R_2$ and $R_3$ can be independently selected from 1) $C_1$–$C_{20}$ alkyl;

2) hydroxy $C_1$–$C_{20}$ alkyl;

3) dihydroxy $C_1$–$C_{20}$ alkyl;

4) poly(oxyethylene) of the formula —$(CH_2CH_2O)_xH$, where x is an integer from 1 to 20;

5) carboxylate esters of d, e, f and g above wherein the acyl chain of the carboxy function is $C_1$ to $C_{20}$ in length and can be saturated or unsaturated;

6) phenyl alkyl (e.g. benzyl or phenethyl);

7) substituted or disubstituted heterocyclic compounds of formula II as defined above; and 8) substituted or disubstituted heterocyclic compounds of formula III as defined above.

Particularly preferred are the compounds:

1) 3-(N, N-dimethylamino)-1,2-propanediol distearate;

2) 3-(N, N-dimethylamino) 1,2-propanediol;

3) 1-(2-hydroxyethyl)-2-oleylimidazoline;

4) N-methyl-N-benzyl-ethanolamine;

5) 1-(2-hydroxyethyl)-2-stearylimidazoline;

6) 1-(2-stearoyloxyethyl)-2-stearylimidazoline;

7) Genamin® T-050 (tallow amine ethoxylate with 5 moles ethylene oxide);

8) Genamin® T-100 (tallow amine ethoxylate with 10 moles ethylene oxide);

9) Genamin® T-200 (tallow amine ethoxylate with 20 moles ethylene oxide);

10) N-methyl-N,N-diethanolamine distearate.

The preparation of the quaternary ammonium methyl sulfates is accomplished by an exothermic process in which the stirred, molten tertiary amine, in a blanket of an inert gas, is reacted with dimethylsulfate. The temperature of the reaction mixture is allowed to reach a point above the melting point of the quaternary amine produced.

Under a blanket of an inert gas, the tertiary amine selected is heated with constant stirring. Depending on which tertiary amine is used, the amine charged into the reaction flask may need to be melted if the starting material is a solid. After heating to about 40° to 80° C., dropwise addition of the dimethylsulfate begins. The tertiary amine must be in a molten state therefore the starting material must be heated at least 5° C. above the melting point; preferably 10°–15° C. above. It is important, however, that the temperature not be raised so high as to thermally degrade the material.

It is critical in the process to keep the molten tertiary amine in an inert atmosphere. Nitrogen or argon are preferred, with nitrogen the most preferred due to its lower cost relative to argon.

As the dimethylsulfate is slowly added, the exothermic nature of the reaction must be monitored. The reaction mixture will become thicker as the reaction continues therefore necessitating constant stirring. When large batches are prepared, the exothermic nature of the reaction results in higher temperatures in the reaction mixture and the dimethylsulfate is added at a lower rate.

The reaction mixture is maintained at about the same temperature during the addition of the dimethylsulfate; that is somewhat above the melting point of the final product. Approximately 0.90 to 0.97 equivalents of the dimethylsulfate are added during the reaction. It is important however to have some free tertiary amine left after the dimethylsulfate is consumed. This is necessary to insure that all of the dimethylsulfate is consumed. After the addition of the dimethylsulfate is complete, the temperature of the reaction mixture is maintained for a period of about 1 to 5 hours or until testing determines that the dimethylsulfate has been completely consumed. When the dimethylsulfate is completely consumed, the reaction is considered to have run to completion.

The degree of completion of the reaction can be determined by calculating the amine number of the solution. This is done utilizing wet analytical techniques that are well known in the art.

The invention will be further illustrated by means of the following examples. The examples are not to be construed as limiting the invention in any manner.

EXAMPLE 1

To a four-necked, 3 liter round bottom flask, equipped with mechanical stirrer, nitrogen purge tube, temperature probe, gas outlet, thermometer and addition funnel, was charged 1273 g (1.9 mol) 1,2-dihydroxy- 3-(N,N-dimethylamino)propane distearyl ester. The free amine was heated to 85°–90° C., and dropwise addition of dimethylsulfate (DMS) (230 g, 1.8 mol) was begun. The addition continued over approximately 35 minutes, during which time the reaction mixture increased to 130° C. The temperature of the reaction mixture was maintained at this temperature for 3 to 4 hours, at which point the amine number of the product was 0.41 ml 0.1N $HClO_4$/g. The reaction proceeded in quantitative yield, based on DMS consumed.

EXAMPLE 2

To a four-necked, 1 liter round bottom flask, equipped as in Example 1, was charged 228.3g of 3-(N,N-dimethylamino)-1,2-propanediol (DMAPD) (1.94 mol). The DMAPD was heated to approximately 55° C with stirring, and dropwise addition of DMS was begun. The addition was carried out over approximately 2.5 hours. The reaction mixture exothermed to approximately 145° C. External cooling was applied to help control the exotherm and the temperature was adjusted to about 115° C. The mixture was stirred at this temperature for approximately one hour, then sampled for amine number: 0.91 ml 0.1N $HClO_4$/g.

EXAMPLE 3

To a four-necked, 1 liter round bottom flask, equipped as in the previous examples, was charged 274.8 g (0.80 mol) 1-(2-hydroxyethyl)-2-oleylimidazoline. The free amine was heated to approximately 80° C., then dropwise addition of DMS (97.3 g, 0.77 mol) was begun. The addition was completed over 45 minutes, during which time the reaction mixture exothermed to 125° C. The reaction mixture was maintained at 125° C. for 5 hours and the final amine number was 0.91 ml 0.1N HClO$_4$/g.

EXAMPLE 4

To a four-necked, 500 ml round bottom flask, equipped as in the previous examples, was charged 149.0 g (0.85 mol) N-methyl-N-benzylethanolamine. The amine was heated to 57° C. with stirring, and dropwise addition of 103.1 g (0.82 mol) DMS was begun. The addition of DMS was carried out over 50 minutes, during which time the reaction mixture exothermed to 130° C. The reaction mixture temperature was adjusted to approximately 120°. The mixture was stirred for 6 hours and sampled for amine number: 1.51 ml 0.1N HClO$_4$/g.

EXAMPLE 5

To a four-necked, 1 liter round bottom flask, equipped as in the previous examples, was charged 316.1 g (0.88 mol) of 1-(2-hydroxyethyl)-2-stearyl-imidazoline. The amine was heated to approximately 70° C. and dropwise addition of DMS (106.1 g, 0.84 mol) was begun. The addition was carried out over 50 minutes, during which time the reaction exothermed to approximately 130° C. The reaction temperature was adjusted to approximately 145° C. The mixture was stirred at this temperature for 2.25 hours, then sampled for amine number: 1.1 ml 0.1N HClO$_4$/g.

EXAMPLE 6

To a four-necked, 3 liter round bottom flask, equipped as in the previous examples, was charged 707.6 g (1.05 mol) 1-(2-stearoyloxyethyl)-2-stearylimidazoline. The amine was heated to 75° with stirring and dropwise addition of 128.1 g (1.01 mol) DMS was begun. The addition was carried out over 45 minutes, during which time the reaction exothermed to 110° C. The temperature of the reaction mixture was maintained between 100°–110° C. for two hours, then sampled for amine number: 0.46 ml 0.1N HClO$_4$/g.

EXAMPLE 7

To a four-necked, 1 liter round bottom flask, equipped as in the previous examples, was charged 300.3 g (0.64 mol) Genamin® T-050 ethoxylate. The amine was heated to 80° C. and dropwise addition of 77.0 g (0.61 mol) DMS was begun. The reaction mixture exothermed to 90° C. during the course of the addition. The reaction temperature was adjusted to 100° C. and the mixture was stirred at this temperature for approximately 3 hours, and then sampled to determine the amine number: 0.61 ml 0.1N HClO$_4$/g.

EXAMPLE 8

To a four-necked, 1 liter round bottom flask, equipped as in the previous examples, was charged 373.2 g (0.52 mol) Genamin® T-100 ethoxylate. The amine was heated to 80° C. and dropwise addition of DMS (59.6 g, 0.47 mol) was begun. The reaction exothermed to 135° C. during the course of the addition. The reaction temperature was adjusted to 135°–140° C. and the mixture was stirred for approximately 2 hours, and then checked for amine number: 1.00 mi. 0.1N HClO$_4$/g.

EXAMPLE 9

To a four-necked, 1 liter round bottom flask, equipped as in the previous examples, was charged 300.0 g (0.25 mol) Genamin® ethoxylate T-200. The amine was heated to 80° C. and dropwise addition of 30.0 g (0.24 mol) DMS was begun. The reaction mixture exothermed to 100° C. during the course of the addition. The reaction temperature was adjusted to 125° C. and the reaction mixture was stirred at this temperature for approximately 3 hours, and then sampled to determine the amine number: 0.54 ml 0.1N HClO$_4$/g.

EXAMPLE 10

To a four-necked, 2 liter round bottom flask, equipped as in the previous examples, was charged 481.8g (0.75 mol) N-methyl-N,N-diethanolamine-distearate. The amine was heated to 85° C. with stirring, then dropwise addition of 91.3 g (0.72 mol) DMS was begun. The addition was carried out over 40 minutes, during which time the reaction mixture exothermed to 110° C. The reaction mixture was starting to gel after addition of three quarters of the DMS charge, so the mixture temperature was increased gradually up to 170° C. After the addition of DMS was complete, the mixture was stirred at 170° C. for 45 minutes, and checked for amine number and discharged: amine number 0.72 ml 0.1N HClO$_4$/g.

Representative examples of tertiary amines which can undergo quaternization by the process of this invention include:

1) ditallow methyl amine;
2) dicoconut methyl amine;
3) dilauryl methyl amine;
4) dimyristyl methyl amine;
5) dipalmityl methyl amine;
6) distearyl methyl amine;
7) dioleyl methyl amine;
8) di(hydrogenated tallow) methyl amine;
9) methyl di(2-hydroxyethyl) amine;
10) methyl di(2-hydroxyethyl) amine mono(tallow ester);
11) methyl di(2-hydroxyethyl) amine mono(cocos ester);
12) methyl di(2-hydroxyethyl) amine mono(stearyl ester);
13) methyl di(2-hydroxyethyl) amine mono(oleyl ester);
14) methyl di(2-hydroxyethyl) amine bis(tallow ester);
15) methyl di(2-hydroxyethyl) amine bis(cocos ester);
16) methyl di(2-hydroxyethyl) amine bis(stearyl ester);
17) methyl di(2-hydroxyethyl) amine bis(oleyl ester);
18) methyl di(2-hydroxypropyl) amine;
19) methyl di(2-hydroxypropyl) amine mono(tallow ester);
20) methyl di(2-hydroxypropyl) amine mono(cocos ester);
21) methyl di(2-hydroxypropyl) amine mono(stearyl ester);
22) methyl di(2-hydroxypropyl) amine mono(oleyl ester);
23) methyl di(2-hydroxypropyl) amine bis(tallow ester);
24) methyl di(2-hydroxypropyl) amine bis(cocos ester);
25) methyl di(2-hydroxypropyl) amine bis(stearyl ester);
26) dimethyl hydroxyethyl amine;
27) dimethyl hydroxyethyl amine tallow ester;
28) dimethyl hydroxyethyl amine cocos ester;

29) dimethyl hydroxyethyl amine stearyl ester;
30) dimethyl hydroxyethyl amine oleyl ester;
31) dimethyl hydroxypropyl amine;
32) dimethyl hydroxypropyl amine tallow ester;
33) dimethyl hydroxypropyl amine cocos ester;
34) dimethyl hydroxypropyl amine stearyl ester;
35) dimethyl hydroxypropyl amine oleyl ester;
36) methyl bis(tallow amidoethyl) (2-hydroxyethyl) amine;
37) methyl bis(hydrogenated tallow am idoethyl) (2-hydroxyethyl) amine;
38) 1-(2-hydroxyethyl)-2-tallow imidazoline;
39) 1-(2-hydroxyethyl)-2-cocos imidazoline;
40) 1-(2-hydroxyethyl)-2-myristyl imidazoline;
41) 1-(2-hydroxyethyl)-2-palmityl imidazoline;
42) 1-(2-hydroxyethyl)-2-stearyl imidazoline;
43) 1-(2-hydroxyethyl)-2-oleyl imidazoline;
44) 1-(2-hydroxypropyl)-2-tallow imidazoline;
45) 1-(2-hydroxypropyl)-2-cocos imidazoline;
46) 1-(2-hydroxypropyl)-2-myristyl imidazoline;
47) 1-(2-hydroxypropyl)-2-palmityl imidazoline;
48) 1-(2-hydroxypropyl)-2-stearyl imidazoline;
49) 1-(2-hydroxypropyl)-2-oleyl imidazoline;
50) 1-(2-tallowoyl oxyethyl)-2-stearyl imidazoline;
51) 1-(2-cocoyl oxyethyl)-2-coconut imidazoline;
52) 1-(2-oleoyl oxyethyl)-2-oleyl imidazoline;
53) 1-(2-myristoyl oxyethyl)-2-myristyl imidazoline;
54) 1-(2-palmitoyl oxyethyl)-2-palmityl imidazoline;
55) 1-(2-stearoyl oxyethyl)-2-stearyl imidazoline;
56) 1-(N-tallowoyl amidoethyl)-2-tallow imidazoline;
57) 1-(N-cocoyl amidoethyl)-2-cocos imidazoline;
58) 1-(N-myristoyl amidoethyl)-2-myristyl imidazoline;
59) 1-(N-palmitoyl amidoethyl)-2-palmityl imidazoline;
60) 1-(N-stearoyl amidoethyl)-2-stearyl imidazoline;
61) 1-(N-oleyl amidoethyl)-2-oleyl imidazoline;
62) 1-(tallowoyl oxypropyl)-2-tallow imidazoline;
63) 1-(cocoyl oxypropyl)-2-coconut imidazoline;
64) 1-(oleoyl oxypropyl)-2-oleyl imidazoline;
65) 1-(myristoyl oxypropyl)-2-myristyl imidazoline;
66) 1-(palmitoyl oxypropyl)-2-palmityl imidazoline;
67) 1-(stearoyl oxypropyl)-2-stearyl imidazoline;
68) 1-(N-tallowoyl amidopropyl)-2-tallow imidazoline;
69) 1-(N-cocoyl amidopropyl)-2-coconut imidazoline;
70) 1-(N-oleoyl amidopropyl)-2-oleyl imidazoline;
71) 1-(N-myristoyl amidopropyl)-2-myristyl imidazoline;
72) 1-(N-palmitoyl amidopropyl)-2-palmityl imidazoline;
73) 1-(N-stearoyl amidopropyl)-2-stearyl imidazoline;
74) benzyl 2-hydroxyethyl methyl amine;
75) benzyl methyl poly(oxyethylated) amine;
76) benzyl lauryl methyl amine;
77) benzyl myristyl methyl amine;
78) benzyl palmityl methyl amine;
79) benzyl stearyl methyl amine;
80) benzyl coconut methyl amine;
81) benzyl tallow methyl amine;
82) benzyl oleyl methyl amine;
83) benzyl di[poly(oxethylated)]amine;
84) benzyl dilauryl amine;
85) benzyl dimyristyl amine;
86) benzyl dipalmityl amine;
87) benzyl distearyl amine;
88) benzyl dicoconut amine;
89) benzyl ditallow amine;
90) benzyl dioleyl amine;
91) dibenzyl 2-hydroxyethyl amine;
92) benzyl poly(oxyethylated) amine;
93) phenethyl methyl poly(oxyethylated) amine;
94) triethanolamine;
95) triethanolamine monolaurate ester;
96) triethanolamine monomyristate ester;
97) triethanolamine monopalmitate ester;
98) triethanolamine monostearate ester;
99) triethanolamine monotallowate ester;
100) triethanolamine monooleate ester;
101) triethanolamine monococoate ester;
102) triethanolamine dilaurate ester;
103) triethanolamine dimyristate ester;
104) triethanolamine dipalmitate ester;
105) triethanolamine distearate ester;
106) triethanolamine ditallowate ester;
107) triethanolamine dioleate ester;
108) triethanolamine dicocoate ester;
109) methyl diethanolamine;
110) methyl diethanolamine monolaurate ester;
111) methyl diethanolamine monomyristate ester;
112) methyl diethanolamine monopalmitate ester;
113) methyl diethanolamine monostearate ester;
114) methyl diethanolamine monotallowate ester;
115) methyl diethanolamine monooleate ester;
116) methyl diethanolamine monococoate ester;
117) tallow di[poly(oxyethylated)]amine;
118) coconut di[poly(oxyethylated)]amine;
119) stearyl di[poly(oxyethylated)]amine;
120) palmityl di[poly(oxyethylated)]amine;
121) myristyl di[poly(oxyethylated)]amine;
122) lauryl di[poly(oxyethylated)]amine; and
123) oleyl di[poly(oxyethylated)]amine.

We claim:

1. A method for the high temperature, solvent free quaternization of tertiary amines of Formula I

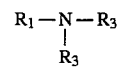

Formula I wherein each of $R_1$, $R_2$ and $R_3$ is independently selected from the group consisting of
a) $C_1$–$C_{20}$ alkyl;
b) $C_2$–$C_{20}$ alkenyl;
c) $C_2$–$C_{20}$ alkynyl;
d) hydroxy $C_1$–$C_{20}$ alkyl;
e) dihydroxy $C_1$–$C_{20}$ alkyl;
f) poly(oxyethylene) of the formula —$(CH_2CH_2O)_xH$, where x is an integer from 1 to 20;
g) poly(oxypropylene) of the formula —$(CH_2CH(CH_3)O)_yH$, where y is an integer from 1 to

50;

h) copolymers of ethylene oxide units of formula —$(CH_2CH_2O)$— and propylene oxide units of formula —$(CH_2CH(CH_3)O)$, wherein said units are (i) arranged randomly, in alternating units or in blocks; and (ii) terminated with —$(CH_2CH_2O)H$ or —$(CH_2CH(CH_3)O)H$; and (iii) the total number of ethylene oxide and propylene oxide units is 2–70;

i) carboxylate esters formed by reacting a moiety selected from the group consisting of hydroxy $C_1$–$C_{20}$ alkyl, dihydroxy $C_1$–$C_{20}$ alkyl, poly(oxyethylene) of the formula —$(CH_2CH_2O)_xH$, where x is an integer from 1 to 20 and poly(oxypropylene) of the formula —$(CH_2CH(CH_3)O)_yH$, where y is an integer from 1 to 50, containing a carboxy function with an acyl portion wherein the acyl portion of the carboxy function contains 1–20 carbons;

j) cyclo $C_3$–$C_8$ alkyl;

k) phenyl and substituted phenyl; and l) phenyl alkyl;

which comprises (1) adding dimethylsulfate to the tertiary amine under a blanket of an inert gas to form a reaction mixture wherein said addition is accomplished at a rate which allows said reaction mixture to attain a temperature which is at least 5 degrees C above the melting point and below a value at which thermal degradation takes place of a final quaternized form of the tertiary amine; and (2) maintaining said temperature until all of the dimethylsulfate is consumed.

2. The method of claim 1 wherein the tertiary amine of Formula I is formed by independently selected $R_1$, $R_2$ and $R_3$ from the group consisting of a) $C_1$–$C_{20}$ alkyl;

b) hydroxy $C_1$–$C_{20}$ alkyl;

c) dihydroxy $C_1$–$C_{20}$ alkyl;

d) poly(oxyethylene) of the formula —$(CH_2CH_2O)_xH$, where x is an integer from 1 to 20;

e) carboxylate esters formed by reacting a moiety selected from the group consisting of hydroxy $C_1$–$C_{20}$ alkyl, dihydroxy $C_1$–$C_{20}$ alkyl, poly(oxyethylene) of the formula —$(CH_2CH_2)_xH$, where x is an integer from 1 to 20 and poly(oxypropylene) of the formula —$(CH_2CH(CH_3)O)_yH$, where y is an integer from 1 to 50, containing a carboxy function with an acyl portion wherein the acyl portion of the carboxy function contains 1–20 carbons; and f) phenyl alkyl.

3. The method of claim 1 wherein the inert gas is selected from nitrogen or argon.

4. The method of claim 3 wherein the inert gas is nitrogen.

5. The method as claimed in claim 1 wherein the reaction takes place in the presence of an excess of the tertiary amines of Formula I.

6. The method of claim 1 wherein the tertiary amine is selected from the group consisting of a) ditallow methyl amine;

b) dicoconut methyl amine;

c) dilauryl methyl amine;

d) dimyristyl methyl amine;

e) dipalmityl methyl amine;

f) distearyl methyl amine;

g) dioleyl methyl amine;

h) di(hydrogenated tallow) methyl amine;

i) methyl di(2-hydroxyethyl) amine;

j) methyl di(2-hydroxyethyl) amine mono(tallow ester);

k) methyl di(2-hydroxyethyl) amine mono(cocos ester);

l) methyl di(2-hydroxyethyl)amine mono(stearyl ester);

m) methyl di(2-hydroxyethyl) amine mono(oleyl ester);

n) methyl di(2-hydroxyethyl) amine bis(tallow ester);

o) methyl di(2-hydroxyethyl) amine bis(cocos ester);

p) methyl di(2-hydroxyethyl) amine bis(stearyl ester);

q) methyl di(2-hydroxyethyl) amine bis(oleyl ester);

r) methyl di(2-hydroxypropyl) amine;

s) methyl di(2-hydroxypropyl) amine mono(tallow ester);

t) methyl di(2-hydroxypropyl) amine mono(cocos ester);

u) methyl di(2-hydroxypropyl) amine mono(stearyl ester);

v) methyl di(2-hydroxypropyl) amine mono(oleyl ester);

w) methyl di(2-hydroxypropyl) amine bis(tallow ester);

x) methyl di(2-hydroxypropyl) amine bis(cocos ester);

y) methyl di(2-hydroxypropyl) amine bis(stearyl ester);

z) dimethyl hydroxyethyl amine;

aa) dimethyl hydroxyethyl amine tallow ester;

bb) dimethyl hydroxyethyl amine cocos ester;

cc) dimethyl hydroxyethyl amine stearyl ester;

dd) dimethyl hydroxyethyl amine oleyl ester;

ee) dimethyl hydroxypropyl amine;

ff) dimethyl hydroxypropyl amine tallow ester;

gg) dimethyl hydroxypropyl amine cocos ester;

hh) dimethyl hydroxypropyl amine stearyl ester;

ii) dimethyl hydroxypropyl amine oleyl ester;

jj) methyl bis(tallow amidoethyl) (2-hydroxyethyl) amine;

kk) methyl bis(hydrogenated tallow amidoethyl) (2-hydroxyethyl) amine;

ll) benzyl 2-hydroxyethyl methyl amine;

mm) benzyl methyl poly(oxyethylated) amine;

nn) benzyl lauryl methyl amine;

oo) benzyl myristyl methyl amine;

pp) benzyl palmityl methyl amine;

qq) benzyl stearyl methyl amine;

rr) benzyl coconut methyl amine;

ss) benzyl tallow methyl amine;

tt) benzyl oleyl methyl amine;

uu) benzyl di[poly(oxyethylated)]amine;

vv) benzyl dilauryl amine;

ww) benzyl dimyristyl amine;

xx) benzyl dipalmityl amine;

yy) benzyl distearyl amine;

zz) benzyl dicoconut amine;

aaa) benzyl ditallow amine;

bbb) benzyl dioleyl amine;

ccc) dibenzyl 2-hydroxyethyl amine;

ddd) benzyl poly(oxyethylated) amine;

eee) phenethyl methyl poly(oxyethylated) amine;

fff) triethanolamine;

ggg) triethanolamine monolaurate ester;

hhh) triethanolamine monomyristate ester;

iii) triethanolamine monopalmitate ester;

jjj) triethanolamine monostearate ester;
kkk) triethanolamine monotallowate ester;
lll) triethanolamine monooleate ester;
mmm) triethanolamine monococoate ester;
nnn) triethanolamine dilaurate ester;
ooo) triethanolamine dimyristate ester;
ppp) triethanolamine dipalmitate ester;
qqq) triethanolamine distearate ester;
rrr) triethanolamine ditallowate ester;
sss) triethanolamine dioleate ester;
ttt) triethanolamine dicocoate ester;
uuu) methyl diethanolamine;
vvv) methyl diethanolamine monolaurate ester;
www) methyl diethanolamine monomyristate ester;
xxx) methyl diethanolamine monopalmitate ester; and
yyy) methyl diethanolamine monostearate ester.

7. The method of claim 1 wherein the tertiary amine is selected from the group consisting of
a) 3-(N,N-dimethylamino)- 1,2-propanediol distearate;
b) 3-(N,N-dimethylamino)- 1,2-propanediol;
c) N-methyl-N-benzyl-ethanolamine;
d) tallow amine ethoxylate with 5 moles ethylene oxide;
e) tallow amine ethoxylate with 10 moles ethylene oxide;
f) tallow amine ethoxylate with 20 moles ethylene oxide; and
g) N-methyl-N,N-diethanolamine distearate.

8. The method of claim 1 wherein the phenyl alkyl moiety is selected from the group consisting of benzyl and phenethyl.

* * * * *